(12) United States Patent
Tseng et al.

(10) Patent No.: US 9,913,466 B2
(45) Date of Patent: Mar. 13, 2018

(54) CRYOPRESERVATION OF UMBILICAL CORD TISSUE STRIPS FOR CORD TISSUE-DERIVED STEM CELLS

(71) Applicant: HealthBanks Biotech Co. LTD., Taipei (TW)

(72) Inventors: Pei-Chi Tseng, Taipei (TW); Xiang-Rui Xu, Taipei (TW); Chi-Hsuan Huang, Taipei (TW); Wei-Yu Lo, Taipei (TW)

(73) Assignee: HealthBanks Biotech Co. Ltd., Taipei (TW)

( * ) Notice: Subject to any disclaimer, the term of this patent is extended or adjusted under 35 U.S.C. 154(b) by 84 days.

(21) Appl. No.: 14/850,810

(22) Filed: Sep. 10, 2015

(65) Prior Publication Data

US 2016/0066566 A1  Mar. 10, 2016

Related U.S. Application Data

(60) Provisional application No. 62/048,762, filed on Sep. 10, 2014.

(51) Int. Cl.

| | | |
|---|---|---|
| *C12N 5/073* | (2010.01) | |
| *A01N 1/02* | (2006.01) | |
| *C12N 5/0775* | (2010.01) | |
| *A61K 35/51* | (2015.01) | |

(52) U.S. Cl.
CPC ............ *A01N 1/0236* (2013.01); *A61K 35/51* (2013.01); *C12N 5/0665* (2013.01)

(58) Field of Classification Search
CPC ..... A01N 1/0236; C12N 5/0665; A61K 35/51
See application file for complete search history.

(56) References Cited

U.S. PATENT DOCUMENTS

| | | | | |
|---|---|---|---|---|
| 8,278,102 B2* | 10/2012 | Ennis | .................... | A01N 1/02 424/583 |
| 8,703,411 B2* | 4/2014 | Chang | .................. | C12N 5/0665 435/1.3 |
| 2009/0275127 A1* | 11/2009 | Ennis | .................... | A01N 1/02 435/366 |
| 2013/0065302 A1* | 3/2013 | Silva | .................... | C12N 5/0605 435/374 |

FOREIGN PATENT DOCUMENTS

| | | | | |
|---|---|---|---|---|
| CN | 102686722 | | 9/2012 | |
| TW | 200613556 | | 5/2006 | |
| TW | 201311145 | | 3/2013 | |
| WO | WO 2007071048 A1 * | 6/2007 | .............. | A01N 1/02 |
| WO | 2008021391 | | 2/2008 | |

OTHER PUBLICATIONS

"Office Action of Taiwan Counterpart Application," dated Jan. 23, 2017, p. 1-p. 5.

* cited by examiner

*Primary Examiner* — Satyendra K Singh
(74) *Attorney, Agent, or Firm* — JCIPRNET

(57) ABSTRACT

A method for cryopreserving an umbilical cord tissue strip includes the steps of: (a) applying tension to a segment of an umbilical cord to expand spaces between umbilical cord vessels; (b) cutting the segment of the umbilical cord, at the spaces between the umbilical cord vessels in a longitudinal direction that parallels a length of the umbilical cord vessels, to obtain the umbilical cord tissue strip, wherein the umbilical cord tissue strip contains Wharton's jelly from a perivascular region, a intervascular region, and a subamnion region; (c) incubating the umbilical cord tissue strip with a cryogenic composition; and (d) cryopreserving the umbilical cord tissue strip containing the Wharton's jelly and the cryogenic composition.

11 Claims, 7 Drawing Sheets

|  | CD13 | CD29 | CD44 | CD73 | CD90 | CD105 | HLA-ABC |
|---|---|---|---|---|---|---|---|
| Control | 99.81% | 99.89% | 99.90% | 99.88% | 99.91% | 99.77% | 99.90% |
| Exp | 99.94% | 99.82% | 99.83% | 99.81% | 99.87% | 99.64% | 99.86% |

|  | CD31 | CD34 | CD45 | HLA-DR | SSEA4 | viability |
|---|---|---|---|---|---|---|
| Control | 2.44% | 2.61% | 2.47% | 2.07% | 51.79% | 95.75% |
| Exp | 1.70% | 1.83% | 1.94% | 2.03% | 58.78% | 95.07% |

CRYOPRESERVATION OF UMBILICAL CORD TISSUE STRIPS FOR CORD TISSUE-DERIVED STEM CELLS

CROSS REFERENCE TO RELATED APPLICATIONS

This claims the benefit of U.S. Provisional Application No. 62/048,762, filed on Sep. 10, 2014, the disclosure of which is incorporated by reference in its entirety.

FIELD OF THE INVENTION

The present invention relates generally to stem cells, and more specifically to methods for preserving umbilical cord tissue-derived stem cells.

BACKGROUND OF THE INVENTION

The potential benefits of preserving a baby's umbilical cord blood are well documented. A similar idea is to preserve a baby's umbilical cord tissue, in which a section of the umbilical cord, together with all the cells contained therein, may be preserved at birth for later use. The cord tissue may be frozen in a cryogenic storage tanks for long-term preservation. When the baby's cells are needed for therapies in the future, the cord tissue may be processed to extract the cells using the best technology available at that time.

For example, U.S. Patent Publication No. 2009/0275127 A1, which is incorporated herein by reference in its entirety, discloses a method for extracting viable progenitor cells from frozen umbilical cord tissues. In this disclosure, an umbilical cord tissue is a blood vessel bearing the perivascular Wharton's jelly, and the extracted progenitor cells are human umbilical cord perivascular cells (HUCPVCs). In the disclosed methods, intact cord vessels with associated Wharton's jelly are obtained by gently pulling the vessels from cord that has been opened longitudinally and sectioned transversely to yield vessel segments. This process sheds the bulk of Wharton's jelly within the cord, but leaves Wharton's jelly in the perivascular region associated with the extracted vessels. The ends of the vessels are tied off to prevent the escape of any blood remaining within the vessels. In the alternative, blood within the vessels can be removed by repeating rinsing.

U.S. Pat. Publication No. 8,703,411 B2, issued to inventors of the present invention, discloses a method of preserving an umbilical cord. The disclosure of the '411 patent is incorporated by reference in its entirety. The method disclosed in the '411 patent comprises obtaining a segment of an umbilical cord; mincing the segment of the umbilical cord into cord tissue pieces; admixing the cord tissue pieces with a cryogenic composition comprising a cryoprotectant and a protein to form a mixture; shaking the mixture for a duration of no shorter than 20 minutes and no longer than 40 minutes; and cryopreserving the mixture.

Umbilical cord tissue preservation and subsequent cell culturing are relatively new techniques. While the prior art provides useful methods for preserving useful umbilical cord tissues, there is still a need for efficient methods that can preserve umbilical cord tissues for later use.

SUMMARY OF THE INVENTION

One aspect of the invention relates to methods for cryopreserving an umbilical cord tissue strip. A method in accordance with one embodiment of the invention comprises the steps of: (a) applying tension to a segment of an umbilical cord to expand spaces between umbilical cord vessels; (b) cutting the segment of the umbilical cord, at the spaces between the umbilical cord vessels in a longitudinal direction that parallels a length of the umbilical cord vessels, to obtain the umbilical cord tissue strip, wherein the umbilical cord tissue strip contains Wharton's jelly from a perivascular region, a intervascular region, and a subamnion region; (c) incubating the umbilical cord tissue strip with a cryogenic composition; and (d) cryopreserving the umbilical cord tissue strip containing the Wharton's jelly and the cryogenic composition.

In accordance with some embodiments of the invention, a method may further comprise cutting the remaining portion of the umbilical cord in the longitudinal direction to obtain two more umbilical cord tissue strips.

In accordance with some embodiments of the invention, in the method, the incubating step may be performed soon after cutting, for example within 5, 6, 7, 8, 9, or 10 minutes from the start of the first cutting, preferably within 6 minutes from the start of the first cutting.

In accordance with some embodiments of the invention, a method may involve using a tool or a probe to apply the tension to the segment of the umbilical cord. One end of the tool or probe may be inserted into a cord vessel, while the other end of the tool or probe may be held or pivotally connected to a stationary device.

In accordance with some embodiments of the invention, a method does not involve digesting the Umbilical cord tissue strip with any enzyme.

In accordance with some embodiments of the invention, the incubating step (c) comprises shaking the cord tissue strips in the cryogenic composition for 20 minutes to 40 minutes.

Another aspect of the invention relates to methods for obtaining umbilical cord tissue-derived stem cells. A method in accordance with one embodiment of the invention comprises (a) thawing a cryopreserved umbilical cord tissue strip that comprises an umbilical cord blood vessel and Wharton's jelly, wherein the Wharton's jelly comprises gelatinous tissue from a perivascular region, a intervascular region, and a subamnion region; (b) removing the cryogenic composition; (c) cutting the umbilical cord tissue strip into cord tissue pieces, wherein the cord tissue pieces are larger than 2 mm in dimension; and (d) culturing the cord tissue pieces in a culture medium to obtain the umbilical cord tissue-derived stem cells. The cord tissue pieces larger than 2 mm in dimension would not pass through a sieve having 2 mm openings. In accordance with some embodiments of the invention, the cord tissue pieces are no smaller than 0.5 cm in dimension.

In accordance with some embodiments of the invention, a method for obtaining umbilical cord tissue-derived stem cells does not comprise treating the umbilical cord tissue strip with enzymatic digestion.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention.

Wherever possible, the same reference numbers are used throughout the drawings to refer to the same or like elements of an embodiment.

DETAILED DESCRIPTION OF THE INVENTION

Figure 1:
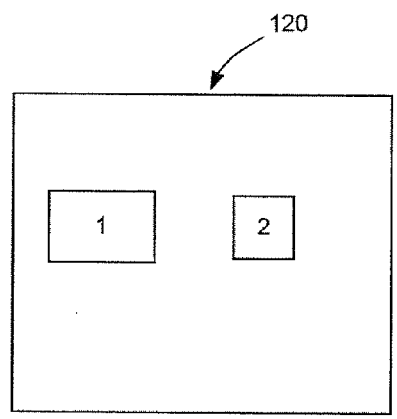
FIG. 1 shows a schematic illustration of an apparatus for immobilizing and cutting an umbilical cord according to one embodiment of the invention.

Embodiments of the present invention are described in the following examples that are intended for illustration only. One skilled in the art would appreciate that other modifications and variations are possible without departing from the scope of the invention. Various embodiments of the invention are described in detail in the following sections, referring to the drawings, in which like numbers indicate like components throughout the views.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein; no special significance is placed upon whether or not a term is elaborated or discussed herein. Synonyms for certain terms are provided. A recital of one or more synonyms does not exclude the use of other synonyms. The use of examples anywhere in this specification, including examples of any terms discussed herein, is for illustration only, and in no way limits the scope and meaning of the invention or of any exemplified term. Likewise, the invention is not limited to the examples given in this specification.

Unless otherwise defined, all technical and scientific terms used herein have the same meaning as commonly understood by one of ordinary skill in the art to which this invention pertains. In the case of conflict, the present document, including definitions will control.

As used herein, "around," "about," or "approximate" shall generally mean within 20 percent, preferably within 10 percent, and more preferably within 5 percent of a given value or range. Numerical quantities given herein are approximate, meaning that the term "around," "about," or "approximately" can be inferred if not expressly stated. Furthermore, any numerical range disclosed herein intends to include all numbers within the range, as if each number within the range has been individually disclosed.

As used herein, "an umbilical cord tissue piece," "cord tissue pieces," and "coarse cord tissue pieces" may be used interchangeably. A coarse cord tissue piece refers to a piece of cord tissue with a size of greater than 2 mm, preferably greater than 3 mm, more preferably greater than 4 mm, and most preferably greater than 5 mm. A cord tissue piece of greater than 2 mm size means that the cord tissue piece cannot pass through a 2 mm sieve of a cell strainer.

As used herein, "a segment of an umbilical cord" refers to a portion of an umbilical cord. A segment of an umbilical cord may be 0.5, 1, 2, 3, 5, 10 cm long or longer, or any numbers therebetween. One skilled in the art would appreciate that the actual length of a segment of an umbilical cord is not important.

"Cryopreservation" or "cryopreserving" is a process wherein cells or whole tissues are preserved by cooling to below freezing temperatures, such as (typically) 77 K or −196° C. (the boiling point of liquid nitrogen). At these low temperatures, any biological activity, including the biochemical reactions that would lead to cell death, is effectively stopped. However, when cryoprotectant solutions are not used, the cells being preserved are often damaged due to freezing during the approach to low temperatures or warming to room temperature.

The terms "freezing" and "cryopreserving" may be used interchangeably. The terms "a cryogenic composition," "a cryogenic solution," "a cryopreservation composition," and "an anti-freezing solution" may be used interchangeably. Any cryogenic composition or cryopreservation composition commonly used in the art may be used. An example of a cryogenic composition or cryopreservation composition may comprise dimethyl sulfoxide (DMSO) at a concentration from about 1% to about 70%, preferably from about 5% to about 55%. Other examples of a cryogenic composition or cryopreservation composition may comprise a cryoprotectant and a protein to form a mixture as disclosed in the '411 patent.

The terms "cord tissue-derived cells," "cord tissue pieces-derived cells," "cord tissue-derived stem cells," and "cord tissue-derived MSCs" may be used interchangeably, unless specified otherwise.

The "doubling time" is the period of time required for a quantity to double in size or value.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

A method for preparing samples of the control group is as disclosed in U.S. Pat. No. 8,703,411 B2. Briefly, an umbilical cord in an appropriate length is cleaned and disinfected. The two arteries are removed, and then the tissues were cut, without in any particular orientation, into pieces with each piece of around 2 mm$^3$. The tissue pieces are treated with enzymatic digestion for an optimal period of time. After the enzymatic reaction is neutralized, tissue pieces are cleaned to remove the residual enzyme, DMSO anti-freezing solution is added, and the tissue pieces are stored in liquid nitrogen. After cryopreservation for more than 1 week, the tissue pieces are thawed, cleaned to remove anti-freezing solution, and cultivated in a primary culture. Depending on the growth conditions, the cells are collected, the cell number is counted, and the cell viability and characteristics are analyzed.

The methods disclosed in the '411 patent are laborious and time-consuming because umbilical cords are slippery and tough to cut. Methods of the present invention are designed to overcome the slipperiness and toughness of the umbilical cord and to make it convenient for a single operator to perform.

In accordance with one embodiment of the invention, a tool that can provide supporting force and fixed force, e.g., forceps, may be inserted into umbilical cord without the need for removing blood vessels therein. In addition, a fixture for holding the umbilical cord in an appropriate position and stretching open the cord may be used to allow a single operator to efficiently cut the cord tissue longitudinally.

An umbilical cord contains three blood vessels, i.e., one vein and two arteries. In accordance with methods of the invention, an umbilical cord may be cut longitudinally into 2 or 3 strips, each containing at least one blood vessel with the associated perivascular Wharton's jelly. Thus, in accordance with embodiments of the invention, a method may take only 2 to 3 cuts to obtain tissue strips with the Wharton's jelly layers fully exposed, allowing the Wharton's jelly layer to directly contact the cryopreservation solution, thereby increasing the efficiency of penetration by a cryopreservation solution into the Wharton's jelly layer tissue. The cryopreservation solution may be directly added to the tissue strips. After mixing with the cryopreservation solution, the tissue strips may be stored in liquid nitrogen.

To demonstrate the viability of the cells preserved by a method of the present invention, after cryopreservation for more than 1 week, the tissue strips were thawed, cleaned to remove anti-freezing solution, and cut into pieces with each piece larger than 2 mm$^3$ (e.g., 2-10 mm$^3$ or preferably 2-5 mm$^3$), and cultivated with the Wharton's Jelly layer facing down (i.e., facing the culture plate bottom) in a primary culture. Depending on the growth conditions, the cells were collected, the cell number was counted, the cell viability and characteristics were analyzed (surface markers analysis and cell viability analysis).

For both the control group (using a method of the '411 patent) and the experimental group (using a method of the present invention), primary UCMSCs were harvested after 10~14 days depending on colony forming unit (CFU) cell growth kinetics. Positive and negative surface markers standing for mesenchymal stem cells (MSCs), early gene SSEA-4 (stage-specific embryonic antigen 4, a cell surface glycosphingolipid gene), and cell viability assayed by 7-aminoactinomycin-D (7-AAD) staining were evaluated by FACS analyses.

Example 1

Preparation of Cord Tissue Strips

FIG. 1 shows a schematic illustrating an example of an apparatus 120 that may be used to immobilize an umbilical cord before cutting the cord to generate cord tissue strips. This is only one example of an apparatus that can facilitate a method of the invention. One skilled in the art would appreciate that other devices may be used as long as it can facilitate the operation of a method of the invention. As shown in FIG. 1, in this example, the apparatus 120 has two slots/holes 1 and 2 that are configured to hold/accommodate tools (such as forceps) used to facilitate the cutting of umbilical cords in accordance with embodiments of the invention.

Figure 2A:
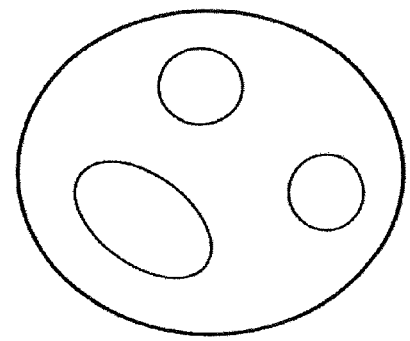
FIG. 2A shows a schematic illustration of an umbilical cord cross section.

FIG. 2A shows a schematic illustrating a cross section of an umbilical cord, which has three blood vessels (one vein 102 and two arteries 104 and 106). An umbilical cord comprises three layers: the amniotic membrane; the umbilical blood vessels, namely two arteries and a vein; and the stroma—a mucous connective tissue known as Wharton's jelly, situated between the amniotic epithelial lining and the umbilical blood vessels. Wharton's jelly can be subdivided into three distinct regions: the subamniotic region (a region proximate the amniotic epithelial lining), the intervascular region (a region between cord vessels) and the perivascular region (in proximate regions surrounding each vessel).

Figure 2B:
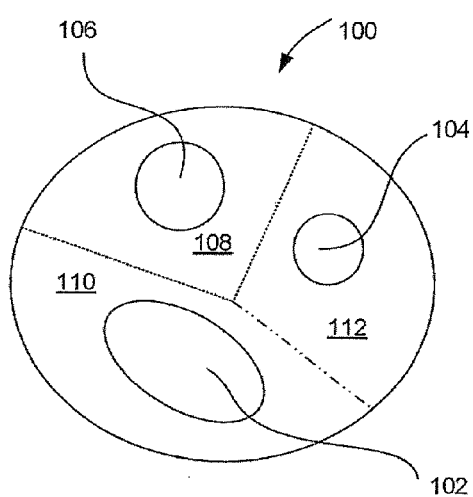
FIG. 2B shows a schematic illustration of an umbilical cord illustrating the preparation of umbilical cord strips according to one embodiment of the invention.

FIG. 2B illustrate a concept in accordance with one embodiment of the invention.

As shown in FIG. 2B, an umbilical cord 100 contains a vein 102 and two arteries 104 and 106. Three cut lines at spaces between cord vessels are shown that will separate these blood vessels intro three cord tissue strips, together with Wharton's jelly around the vessels. The Wharton's jelly contained in each cord tissue strip thus obtained would include Wharton's jelly from all three regions: subamniotic zone, the intervascular zone and the perivascular zone. In this example, vein 102 together with the surrounding Wharton's jelly layer forms a strip 110. Artery 104 together with the surrounding Wharton's jelly layer forms another strip 112. Artery 106 together with the surrounding Wharton's jelly layer forms yet another strip 108.

Figure 2C:
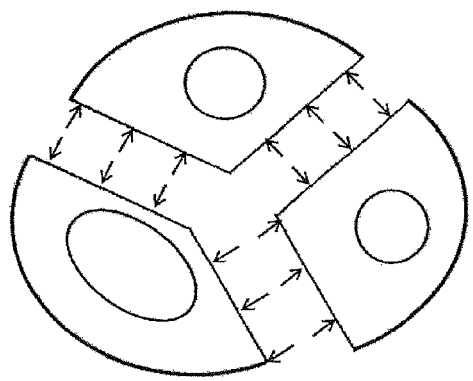
FIG. 2C shows a schematic illustration of cord strips incubating with a cryopreservation solution.

Once these cord strips are separated, more surfaces of Wharton's jelly are exposed, as shown in FIG. 2C. The greater exposed surface area of the Wharton's jelly facilitates the permeation of the cryopreservation solution into the cord strips. Therefore, cells in the cord strips are less likely to be damaged during freezing and thawing processes. As a result, more viable cells can be recovered from such cryopreserved cord strips.

Methods of the invention are designed to swiftly cut the cord and in the meantime to increase the Wharton's jelly layer's contact area with the cryopreservation solution. Tools (e.g., a pair of forceps) with supporting force and fixed force that were able to hold and fix the cord may be used.

For example, referring to FIGS. 2A-2C, one end of a tool (e.g., a pair of forceps) may be inserted into the lumen of a blood vessel (such as, the umbilical cord vein 102) of a segment of an umbilical cord 100. Then, the other end of the same tool may be fixed on an apparatus, such as inserting into the slot/hole 1 on an umbilical cord-immobilizing instrument/apparatus 120 (FIG. 1). In a similar process, one end of a second tool is inserted into the lumen of a second blood vessel (such as the umbilical cord artery 104). The other end of the second tool is then fixed at slot 2 on the umbilical cord-immobilizing instrument/apparatus 120 (FIG. 1).

Similarly, one end of a third tool may be inserted into the lumen of the third blood vessel (such as the umbilical cord artery 106). Then, a slight tension may be applied to the cord (via the inserted tools) to stretch open the space between the blood vessels, i.e., the umbilical cord artery 106, the umbilical cord vein 102, and the umbilical cord artery 104.

While the umbilical cord is under tension, a cutting tool (e.g., a surgical knife) may be used to cut through the Wharton's Jelly located between the blood vessels, such as between the umbilical cord artery 106 and the umbilical cord vein 102, in a longitudinal direction that parallels the length of the cord vessels. Then, a second cut in the longitudinal direction may be made at a space between the umbilical cord artery 106 and the umbilical cord artery 104, to obtain a cord strip 108 containing umbilical cord artery 106.

Similarly, cord strips 110 and 112 may be obtained by further cutting. For example, while applying tension to the remaining cord to open up the Wharton's jelly between the umbilical cord vein 102 and the umbilical cord artery 104, a further cut may be made through the Wharton's jelly there and split the remaining cord into two cord strips 110 and 112.

Please note that the above example describes inserting the tools and cutting the cord strips in a certain order. This is for clarity of illustration. One skilled in the art would appreciate that other orders of tool insertions and cuttings may be used without departing from the scope of the invention. In addition, while the tools are inserted into lumens of blood vessels in the above description. It is also possible to insert the tools into Wharton's jelly layers proximate the blood vessels. One skilled in the art would appreciate that insertion of the tools is to apply slight tension to open up the space between the blood vessels and/or to straighten the segment of the umbilical cord to facilitate the cutting operations. Therefore, whether the tools are inserted into lumens of the blood vessels is not critical.

Once the cord strips are obtained, these cord strips will be washed, disinfected, and then soaked with a cryopreservation solution to prevent damages to the cells during freezing and thawing processes. For example, the cord strips 108, 110, and 112 may be placed in a tube containing a disinfectant solution for a suitable duration (e.g., 30 seconds to a few minutes) to wash the cord strips. These cord strips may then be washed with a buffer solution to remove impurities.

The cord strips 108, 110 and 112 are then incubated with a cryopreservation solution by shaking for a suitable duration (e.g., 20-60 minutes) at a low temperature (e.g., below 10° C.). The incubation of the cord strips with a cryopreservation solution should be performed soon after cutting, for example within 5, 6, 7, 8, 9, or 10 minutes from the start of the first cutting; preferably within 6 minutes from the start of the first cutting. Finally, the cord strips 108, 110 and 112 may be slowly frozen at a suitable temperature (e.g., −70° C.), followed by cryopreservation in a liquid nitrogen tank with an ultra-low storage temperature (e.g., below −120° C.).

Figure 3:
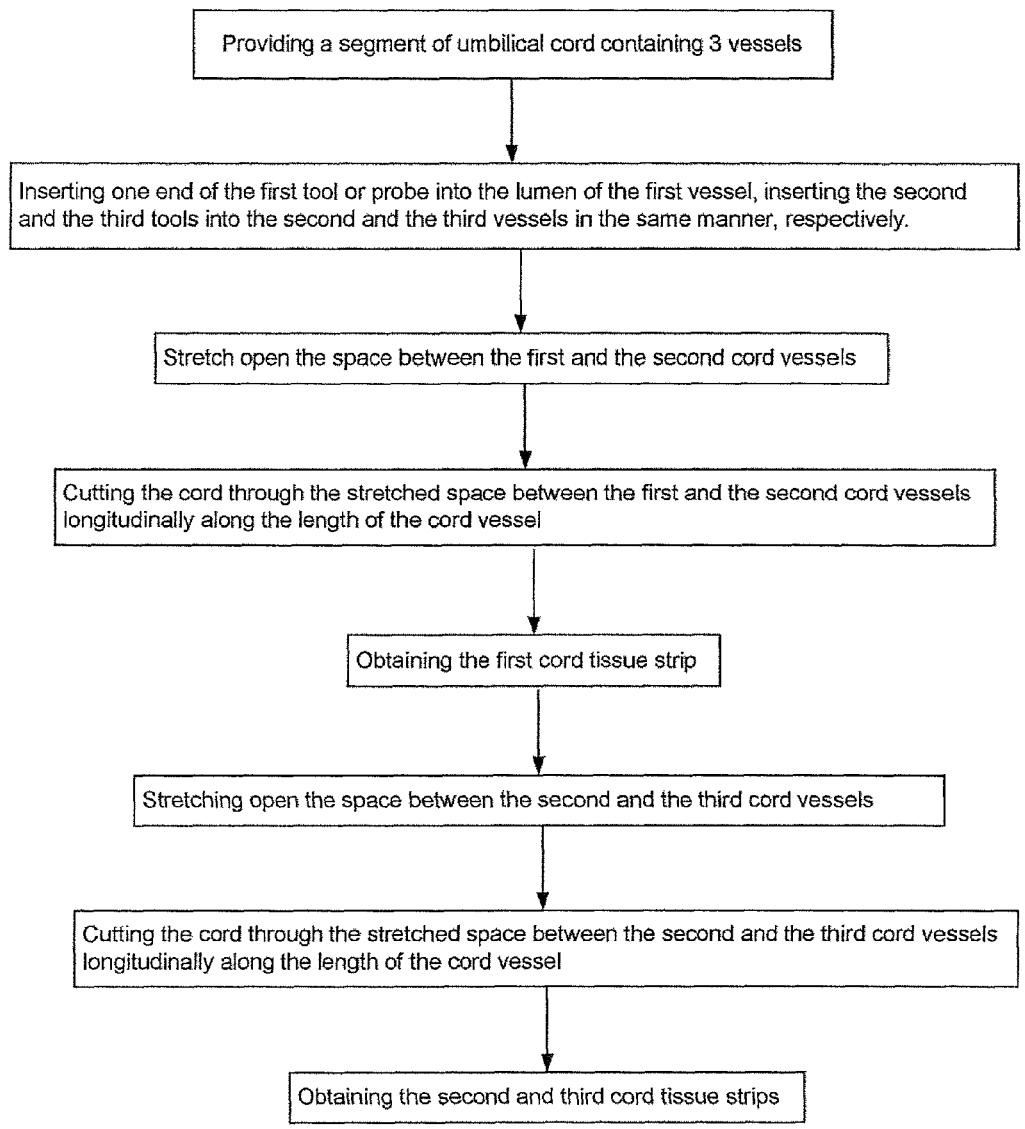
FIG. 3 shows a flowchart illustrating a procedure for processing an umbilical cord for cryopreservation in accordance with one embodiment of the invention.

FIG. 3 is a flowchart that illustrates one of the embodiments of the invention. It shows the process of preparing umbilical cord tissue strips for cryopreservation. A segment of an umbilical cord in an appropriate length (for example, about 3 cm, 5 cm, 7 cm or 10 cm, preferably 3-7 cm), the cord containing three vessels. One or more tools are inserted into the lumens of the cord vessels as described above. A gentle force is applied to stretch open the Wharton Jelly layer (the first space) between the first and the second vessels, and then a surgical knife may be used to cut through the first space in a longitudinal direction (i.e., parallel to the vessels). Then, a second cut is made through the Wharton Jelly layer (the second space) between the first and the second vessels in the longitudinal direction to obtain the first cord strip. Afterwards, stretch open the Wharton Jelly layer (the third space) between the second and the third vessels, and cut through the third space in the longitudinal direction (parallel to the vessels) to obtain the second and the third cord strips.

Figure 4A:
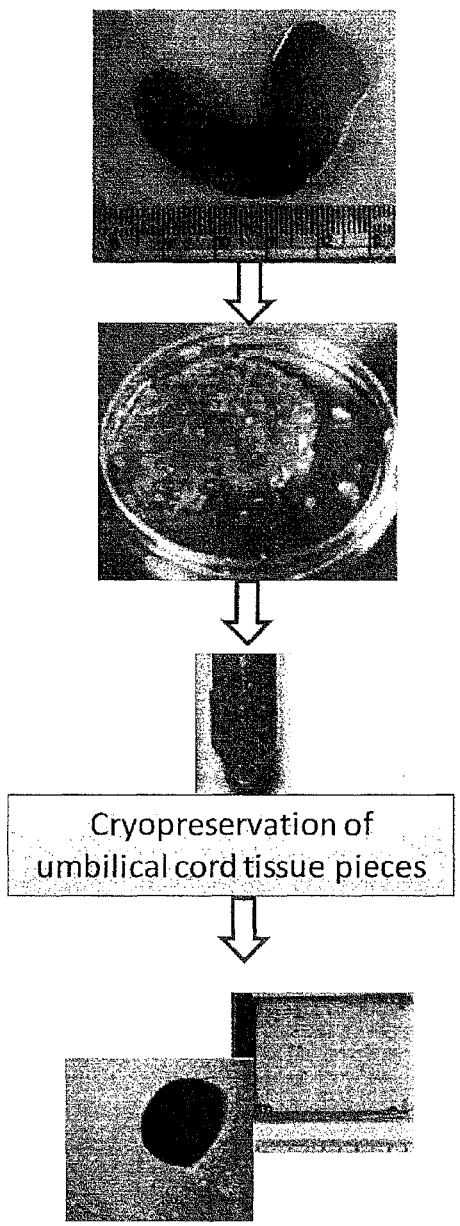
FIG. 4A shows photographs illustrating a process for treating an umbilical cord for cryopreservation, thawing and culturing the preserved umbilical cord to obtain primary UC-MSCs according to a method of U.S. Pat. publication No. 8,703,411 B2.
Figure 4B:
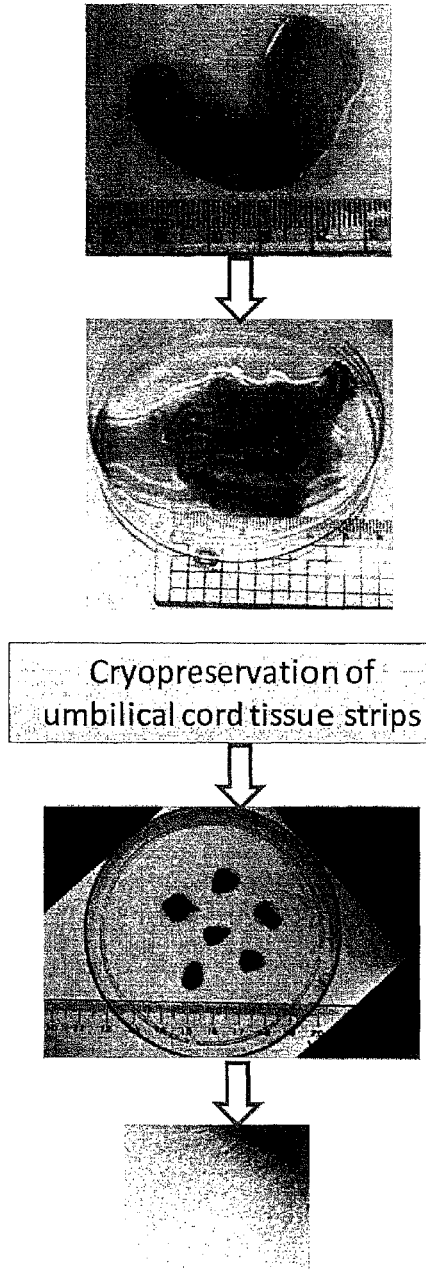
FIG. 4B shows photographs illustrating a process for treating an umbilical cord for cryopreservation, thawing, cutting the strips into coarse pieces, and culturing to obtain primary UC-MSCs in accordance with one embodiment of the invention.

FIGS. 4A-B are photographs that illustrate the differences in the process for preparation of cord tissues for cryopreservation between the prior art method (FIG. 4A: Control group, see U.S. Pat. No. 8,703,411 B2) and the instant invention (FIG. 4B: experimental group).

FIG. 4A (prior art) shows a segment of umbilical cord was disinfected, cleaned, two arteries therein removed, and then manually cut the cord tissue repetitively into pieces with each piece of about 2 mm without regard to any particular orientation. Then, the pieces are subjected to enzymatic digestion for about 20-40 minutes, and then the digestion solution is added into a serum-containing medium or enzyme-neutralizing reagent to stop enzymatic digestion. The pieces are washed with buffer or cell culture medium (e.g., DMEM), subjected to low speed centrifuge to spin down the tissue pieces and remove the residual enzyme. The tissue pieces are then mixed with a cryopreservation solution by shaking at a temperature no greater 10° C. for 20-60 minutes, and then stored at an ultralow temperature in liquid nitrogen.

To test viabilities of the cryopreserved cells, after more than one week of cryopreservation, a sample of the tissue pieces is quickly thawed at 37° C., washed several times, and subjected to low speed centrifuge to spin down the tissue pieces and completely remove cryopreservation solution. Then, the tissue pieces were cultivated for primary culture, and the cells were collected after 10-14 days, depending on the cell growth condition.

FIG. 4B illustrates an example of the instant invention, showing a segment of umbilical cord was disinfected, cleaned, and cut into several long thin cord tissue strips (i.e., cord strips described above) without the need to first remove the cord vessels. Then, the cord strips are mixed (e.g., by shaking) with a cryopreservation solution at a suitable temperature (no greater than 10° C., such as 0-10° C.) for a suitable duration (e.g., 20-60 minutes, preferably 30-50 minutes). Then, the cord strips are stored at an ultralow temperature (e.g., in liquid nitrogen).

To test the viability of cells in the cryopreserved cord strip, after more than one week of cryopreservation, a cord strip is quickly thawed at 37° C., washed several times, and centrifuged at a low speed to spin down the tissue pieces. After completely removing the cryopreservation solution, the tissue strips were cut into tissue chunks (coarse tissue pieces) with each tissue chunk larger than 2 mm (e.g., 5 mm) in dimension with a sharp tool (e.g., scissors or surgical knife). The tissue chunks were cultivated for primary culture. Depending on the cell growth conditions, cells were collected after 10-14 days.

Figure 4C:
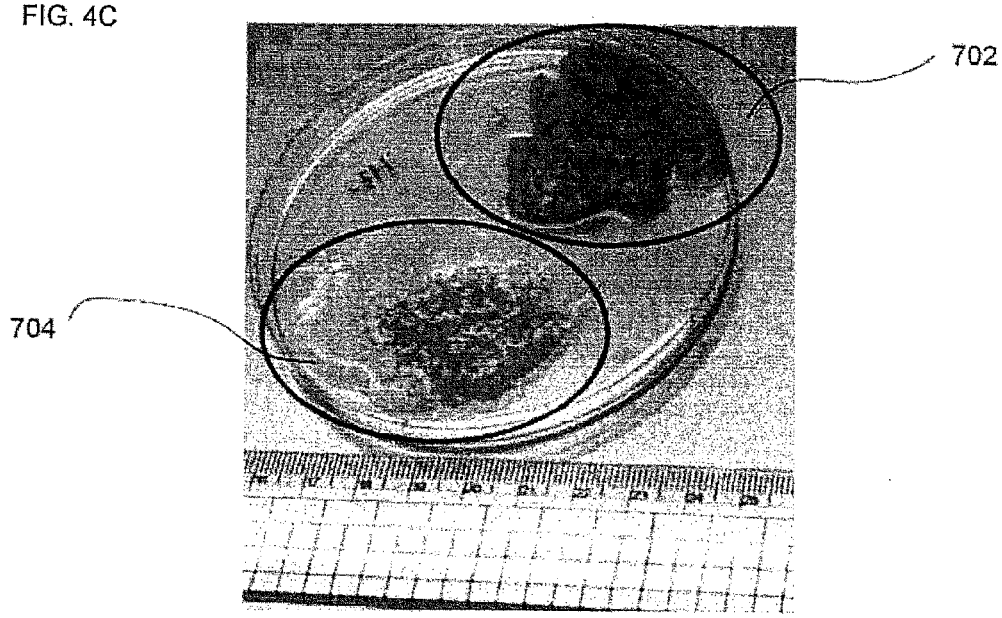
FIG. 4C shows a photograph comparing the sizes of the cord tissue pieces for culturing UC-MSCs disclosed in U.S. Pat. publication No. 8,703,411 B2 with the sizes of the same obtained with a method of the present invention.

FIG. 4C is a photograph illustrating the difference in size between the tissue pieces 704 and tissue chunks 702.

Figure 5A:
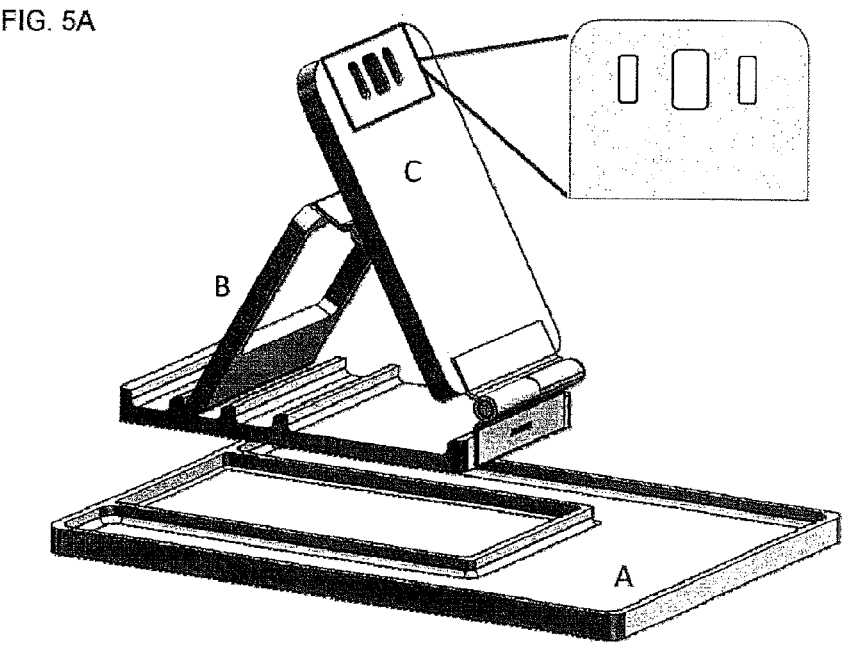
FIG. 5A shows a schematic illustrating an example of an instrument designed to immobilize and position an umbilical cord in a manner that is easy for processing the cord to generate cord tissue strips for cryopreservation according to one embodiment of the invention.
Figure 5B:
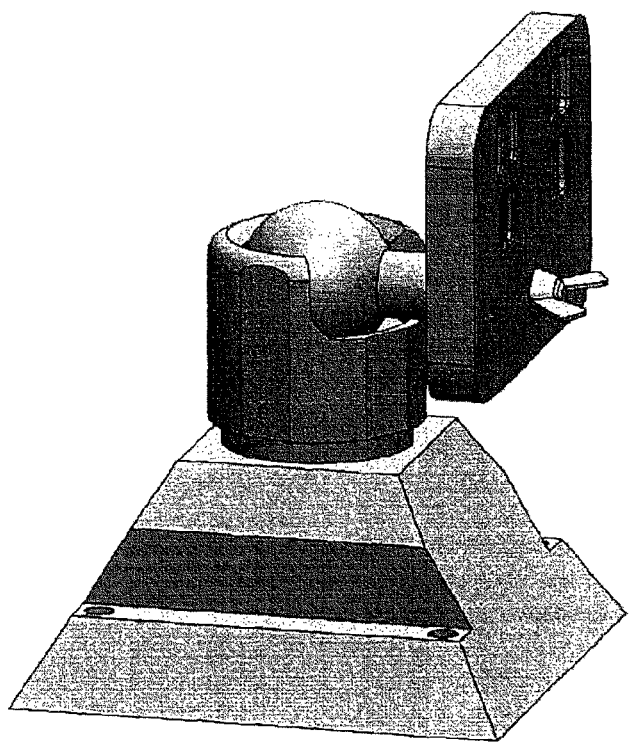
FIG. 5B shows a schematic illustrating another example of an instrument designed to immobilize and position an umbilical cord in a manner that is easy for processing the cord to generate cord tissue strips for cryopreservation according to an embodiment of the invention.
Figure 5C:
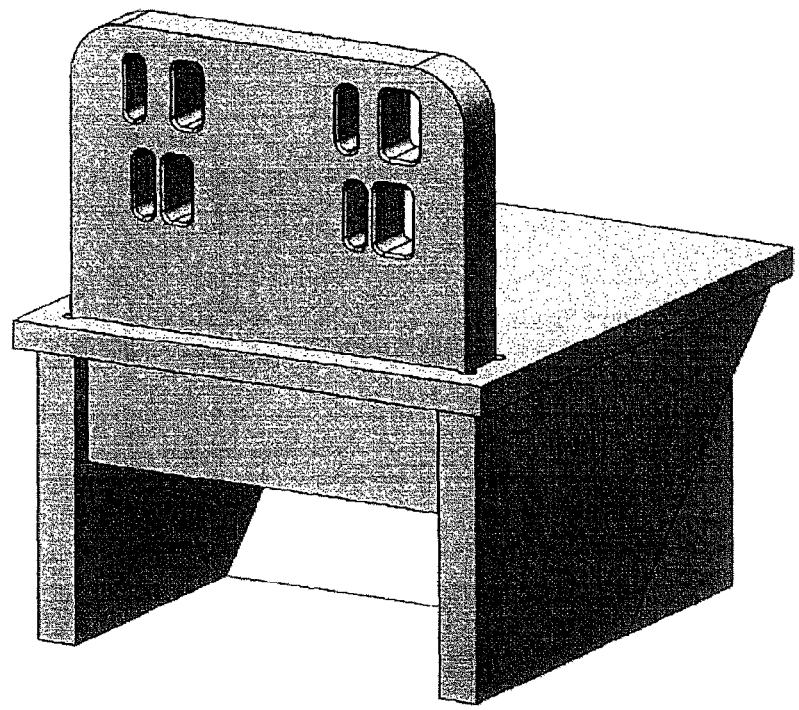
FIG. 5C shows a schematic illustrating another example an instrument designed to immobilize and position an umbilical cord in a manner that is easy for processing the cord to generate cord tissue strips for cryopreservation according to one embodiment of the invention.

FIGS. 5A-C illustrate various examples of apparatus that may be used to immobilize an umbilical cord to facilitate the cutting operation in accordance with embodiments of the invention. The apparatus was designed for simplicity, convenience, one-man operation, and minimal contamination. The apparatus in FIG. 5A comprises the following components:

(i) a base, having a top surface and a bottom surface, and a front end and a rear end, the top surface near the front end comprising raised ridges, the ridges being evenly spaced apart;

(ii) a stand having a top surface and a bottom surface, and a front and a rear end, the top surface near the front end comprising one or more slots, each being adapted for receiving the an end of a tool or probe, and the rear end being operatively connected to the rear end of the base;

(iii) a prop, having a top and bottom end, and a front surface and a rear surface, the top end being operatively connected to the bottom surface of the stand, and the bottom end being slidably coupled to the top surface of the base and located between the ridges; and (iv) a trough, movably coupled to the bottom surface of the base.

The apparatus shown in FIG. 5A is just one example. One skilled in the art would appreciate that many modifications and variations of such an apparatus may be used with methods of the invention. For example, FIG. 5B shows another example of an apparatus that may be used with a method of the invention. The apparatus in FIG. 5B comprises the following components:

(i) a base, having a top surface and a bottom surface, and a front end and a rear end, a screw fixed on the top surface of the base, a ball holding chamber formed on the top of the screw, and the stand has a screw hole;

(ii) a stand, having a top surface and a bottom surface, and a front and a rear end, the top surface near the front end comprising at least 2 slots, each being adapted for receiving an end of the tool or the probe;

(iii) a connection part, having a ball end detachably and rotatably coupled to the ball holding chamber and a near end with a threaded hole;

(iv) a screw hollow cap, having a top end and a bottom end with opening apertures on both end and an opening on the lateral side being connected to the opening aperture of the top end, the screw hollow cap being mounted on the screw and the ball end of the connection part being located inside the screw hollow cap, and the opening aperture of the top end smaller than the ball end just for the screw hollow cap screwing to the screw to lock the ball end and then the near end of the connection part protruding from the top opening aperture and the lateral opening; and (v) a screw nut, having one end passing through the screw hole to threaded hole for fixing the stand.

FIG. 5C shows another example of an apparatus that may be used with a method of the invention. The apparatus in FIG. 5C comprises the following components:

(i) a base, being a hollow rectangular box structure without bottom surface, which includes a top wall and two lateral walls perpendicular to the top wall, the lateral walls having same trapezium shapes with two parallel sides respectively, the longer parallel sides connected to the top wall and another shorter parallel sides standing on a platform to hold the stack in a perpendicular position, furthermore, each of the lateral walls having sloping sides respectively standing on the platform to hold the stack in an inclined position;

(ii) a stand, having a top surface and a bottom surface, and a front end and a rear end, the top surface near the front end comprising at least 2 slots, each being adapted for receiving the other end of the tool or the probe;

(iii) a transverse slot, being formed on the top wall for fitting the stand; and (iv) two vertical grooves, being formed on inner surfaces of the lateral walls downward from the transverse slot for holding the stand.

To investigate the effects of the lengths of the cord tissue strips and the sizes of tissue chunks cut from the cord tissue strips after thawing the cord tissue strips on the cell cultures, the following experimental groups shown in Table 1 are tested. The lengths of cord tissue strips tested range from 0.5 cm to 10 cm. After thawing, tissue chunks with a size ranging from 0.5 cm to 10 cm are grown in tissue culture. The cell numbers and culture results were compared between groups. It is found that an umbilical cord tissue strip having a length of 1-10 cm produce excellent results. However, a length outside of this range may also be used because very good results are still obtained. A preferred range of length for an umbilical cord tissue strip is from 3-7 cm.

Example 2

Comparisons of the Invention with Prior Art Method

Figure 6A:
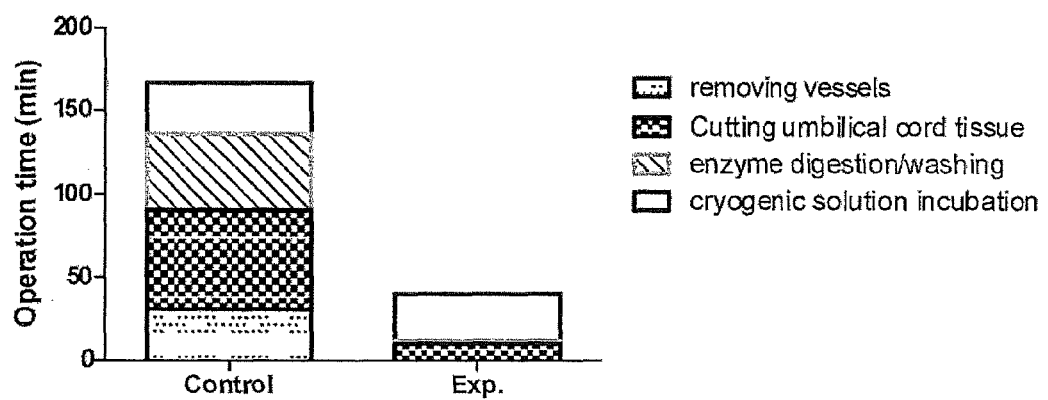
FIG. 6A shows a graph comparing the operation times before cryopreservation between the control group (according to a method of the '411 patent) and experimental group (according to a method of the present invention).

FIG. 6A shows a graph comparing the difference in operation times between the prior art method and a method of the instant invention. The operation time is that needed to prepare cord tissues for cryopreservation. The method of preparation is as described in example 1. The invention (experimental group) saves times, does not need to remove blood vessels (about 30 minutes), has no need for enzymatic digestion and neutralization and washing enzyme away (about 45 minutes). The novel cutting style/method saves time in cutting umbilical cord tissues (the control group needs 60 minutes versus the experimental group needs 10 minutes). Overall, a method of the invention can saves about 125 minutes.

In comparison with methods disclosed in prior art, methods of the invention may have one or more of the following advantages: simple, fast, increasing cell culture efficiency, raising primary culture cell yield, and minimizing variations caused by human factors.

Figure 6B:
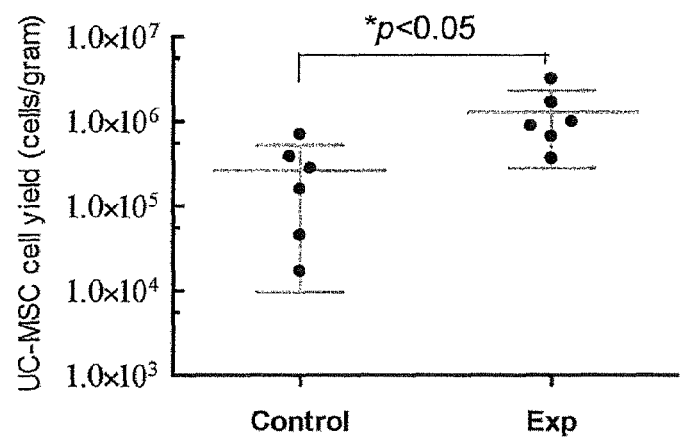
FIG. 6B shows a graph illustrating the cell numbers of UC-MSCs per gram of the cord tissue in the primary culture of the control group (according to a method of the '411 patent) and experimental group (according to a method of the present invention).

FIG. 6B is a graph showing a comparison of cell yields between the control and experimental groups. The tissues in the control and experimental groups were obtained from the same umbilical cord. The cell yields were calculated as follows: the total cell number collected divided by the primary cell culture tissue weight (i.e., cell number per gram of tissue). The cell yield of the primary cell culture in the control group was $2.6 \times 10^5 \pm 2.5 \times 10^5$ (mean±SD), and in the experimental group was $1.3 \times 10^6 \pm 1.0 \times 10^6$ (mean±SD). Using paired t-test statistics to analyze the results, the experimental group cell yield was 5 times that of the control group, with statistical significance, *$p<0.05$ (n=6). In addition, compared to the control group, the experimental group in the primary culture cell yield showed less variations among individual experiments (Control: CV %=96.34%; Exp. CV %=77.93%).

With regard to saving time for growing primary cell culture, the experimental group could save 1.8 days (FIG. 6C, control: 12.83±2.71 days; experimental group: 11±0.89 days) (mean±SD). Both groups could obtain umbilical cord mesenchymal stem cell (UC-MSC) cell viability and purity with a good quality and without differences.

Figures 6C, 6D:
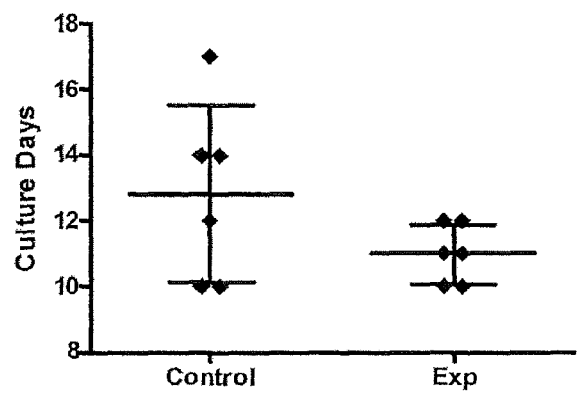
FIG. 6C shows a graph illustrating the primary culture days of the control group (according to a method of the '411 patent) and experimental group (according to a method of the present invention).
FIG. 6D shows a table comparing the positive and negative MSC surface markers expression levels, as well as cell viability, between the control group (according to a method of the '411 patent) and experimental group (according to a method of the present invention).

FIG. 6D illustrates the results of cell surface antigen marker analyses. The results were in compliance with ISCT regulations of MSCs: positive markers (such as CD13, CD29, CD44, CD73, CD90, CD105, and HLA-ABC)>95% and negative markers (such as CD31, CD34, CD45, and HLA-DR)<2%. The stem cell early stage marker SSEA4 was expressed in both groups and the amounts of expression were very similar. Primary UC-MSC cell viabilities in both groups were all greater than 95%.

Therefore, the experimental group has advantages of time-saving, simplicity and convenience, lower irregular size difference caused by manual operations, avoiding or minimizing mechanical damages caused by mincing the tissue into small pieces, and at the same time increasing the Wharton's Jelly layer surface area exposed to the cryopreservation solution. The frozen tissue viability is thus high, which permits subsequent processing to obtain tissue chunks for primary culture with increased cell yields.

While the invention has been described with respect to a limited number of embodiments, those skilled in the art, having benefit of this disclosure, will appreciate that other modifications and variations are possible without departing from the scope of the invention as disclosed herein. Accordingly, the scope of the invention should be limited only by the attached claims.

What is claimed is:

1. A method for cryopreserving an umbilical cord tissue strip, comprising the steps of:
    (a) applying tension to a segment of an umbilical cord to expand spaces between umbilical cord vessels;
    (b) cutting the segment of the umbilical cord, at the spaces between the umbilical cord vessels in a longitudinal direction that parallels a length of the umbilical cord vessels, and obtaining the umbilical cord tissue strip, wherein the umbilical cord tissue strip comprises Wharton's jelly from a perivascular region, an intervascular region and a subamnion region;
    (c) incubating the umbilical cord tissue strip with a cryogenic composition; and
    (d) cryopreserving the umbilical cord tissue strip containing the Wharton's jelly and the cryogenic composition, wherein the method does not comprise isolating, pulling away or removing the umbilical cord vessels from the umbilical cord.

2. The method of claim 1, prior to step (c) further comprising:
    (b') cutting the remaining portion of the umbilical cord in the longitudinal direction to obtain two more umbilical cord tissue strips.

3. The method of claim 2, wherein the incubating step is performed within 5, 6, 7, 8, 9, or 10 minutes from the start of the first cutting.

4. The method of claim 2, wherein the incubating step is performed within 6 minutes from the start of the first cutting.

5. The method of claim 1, wherein step (a) comprises: using a tool or a probe to apply the tension to the segment of the umbilical cord.

6. The method of claim 1, prior to step (a) further comprising:
    inserting one end of a tool or a probe into a lumen of an umbilical cord vessel.

7. The method of claim 6, wherein the other end of the tool or the probe is held or pivotally connected to a stationary device.

8. The method of claim 1, wherein the method does not comprise treating the umbilical cord tissue strip with enzymatic digestion.

9. The method of claim 1, wherein step (c) comprises shaking the cord tissue strips in the cryogenic composition for 20 minutes to 40 minutes.

10. The method of claim 1, wherein in the culturing incubating step the Wharton's jelly of the umbilical cord tissue strip faces down.

11. The method of claim 1, wherein the method does not comprise mincing the umbilical cord tissue strip into tissue pieces having a size of less than 0.5 cm per piece.

* * * * *